(12) United States Patent
Sambu

(10) Patent No.: US 10,894,875 B2
(45) Date of Patent: Jan. 19, 2021

(54) FILMS AND UNIT DOSE ARTICLES COMPRISING AVERSIVE UV-PROTECTIVE AGENTS, AND USES AND METHODS RELATED THERETO

(71) Applicant: The Procter & Gamble Company, Cincinnati, OH (US)

(72) Inventor: Sammy Kibet Sambu, Brussels (BE)

(73) Assignee: The Procter & Gamble Company, Cincinnati, OH (US)

( * ) Notice: Subject to any disclaimer, the term of this patent is extended or adjusted under 35 U.S.C. 154(b) by 142 days.

(21) Appl. No.: 16/207,229

(22) Filed: Dec. 3, 2018

(65) Prior Publication Data

US 2019/0185637 A1 Jun. 20, 2019

(30) Foreign Application Priority Data

Dec. 14, 2017 (EP) .................................... 17207373

(51) Int. Cl.
| | |
|---|---|
| *C11D 17/04* | (2006.01) |
| *C11D 3/37* | (2006.01) |
| *B65D 65/46* | (2006.01) |
| *C07D 455/02* | (2006.01) |
| *C08J 5/18* | (2006.01) |
| *C08K 5/3432* | (2006.01) |
| *C11D 3/39* | (2006.01) |

(52) U.S. Cl.
CPC ............ *C08K 5/3432* (2013.01); *B65D 65/46* (2013.01); *C07D 455/02* (2013.01); *C08J 5/18* (2013.01); *C11D 3/3753* (2013.01); *C11D 3/392* (2013.01); *C11D 17/042* (2013.01); *C11D 17/043* (2013.01); *C11D 17/045* (2013.01); *C08J 2329/04* (2013.01)

(58) Field of Classification Search
None
See application file for complete search history.

(56) References Cited

U.S. PATENT DOCUMENTS

| | | | |
|---|---|---|---|
| 5,783,541 A | 7/1998 | Tack et al. | |
| 9,403,818 B2 * | 8/2016 | Heim ...................... | A61K 38/12 |
| 2007/0032621 A1 * | 2/2007 | Schulte ..................... | C08F 8/12 |
| | | | 526/330 |
| 2011/0250754 A1 * | 10/2011 | Hirano ..................... | C09G 1/18 |
| | | | 438/693 |
| 2016/0376263 A1 * | 12/2016 | Patron .................. | C07D 413/14 |
| | | | 514/784 |
| 2017/0067003 A1 | 3/2017 | Souter et al. | |
| 2017/0096418 A1 * | 4/2017 | Patron ..................... | A23L 33/10 |

OTHER PUBLICATIONS

H. Ihmels , "Product Class 7: Quinolizinium Salts and Benzo Analogues", Science of Synthesis, 2005, vol. 15, pp. 907-945.*
CM4929 EP Search report for application No. 17207373.6-1106, dated May 17, 2018, 8 pages.
Frank et al.—"Reinvestigation ofthe Chemical Structure of Bitter-TastingQuinizolate and Homoquinizolate andStudies on Their Maillard-Type FormationPAthyways Using Suitable 13 C-LabelingExperiments",Journal of Agricultural and FoodChemi Stry, vo 1. 50, No. 21, Oct. 1, 2002 (Oct. 1, 2002), pp. 6027-6036, XP055473170,USISSN: 0021-8561, 001: 10.1021/JF020473k.

* cited by examiner

*Primary Examiner* — Lorna M Douyon
(74) *Attorney, Agent, or Firm* — Gregory S. Darley-Emerson

(57) ABSTRACT

Films including an aversive UV-protective agent, e.g., a quinoliziumolate, exhibiting improved thermostable UV protection and an acceptable bittering value at the same time which further minimizes processing complexity. Unit dose articles that include such films. Related processes.

20 Claims, No Drawings

FILMS AND UNIT DOSE ARTICLES COMPRISING AVERSIVE UV-PROTECTIVE AGENTS, AND USES AND METHODS RELATED THERETO

FIELD OF THE INVENTION

The present disclosure relates to films comprising an aversive UV-protective agent. The present disclosure further relates to unit dose articles comprising such films. The present disclosure further relates to methods of making and using such films and unit dose articles.

BACKGROUND OF THE INVENTION

Water-soluble unit dose articles are becoming increasingly popular with consumers as they offer effective and efficient means of dosing appropriate levels of detergent or cleaning compositions to the wash. The water-soluble unit dose articles typically come in the form of small pouches made of water-soluble films, where the pouches contain concentrated detergent or cleaning compositions. Such films must be selected for a variety of processing and performance criteria, such as thermoformability, sealability, and dissolution properties. A common commercially available film is a polyvinyl alcohol film called M8630 film available from MonoSol, LLC (Merrilville, Ind., USA).

Once in the hands of consumers, the water-soluble unit dose articles can be exposed to high temperatures and UV-light upon storage, especially in geographies such as the Middle East and Africa. Because water-soluble films are prone to degradation upon UV-light exposure, UV-protective agents can be added to the water-soluble film of the unit dose article. As such, the risk on film cracking, eventually leading to leakage of the detergent or cleaning composition out of the pouch can be reduced.

However, traditional UV-protective agents are thermosensitive and degrade at high temperatures. To avoid degradation of such UV-protective agents, the processing temperature of water-soluble films comprising such UV-protective agents is limited. However, as heating is required for efficient film thermoforming and film sealing, a lower processing temperature makes it more difficult to deform the film into a pouch and increases the risk on leakage of the detergent or cleaning composition out of the pouch. Furthermore, exposure to humidity during supply chain can initiate hydrolytic degradation of the UV-protective agent alongside thermal degradation.

Additionally, there is a desire to add aversive agents to water-soluble unit dose article to reduce likelihood of accidental ingestion. Such aversive agents could be substances that provide a bitter taste to the unit dose article and so elicit an instinctive impulse to spit the unit dose article out of the mouth. Denatonium benzoate is a well-known effective aversive agent.

However, those regions that require UV-protective agents, increased processing and cost complexity arises when both aversive agents and UV-protective agents are separately added to the water-soluble film. Moreover, the addition of two separate materials to the film can destabilize the elasticity and water solubility of the film.

Therefore, there is a need for a water-soluble film and unit dose articles comprising such films that provide aversive properties, and resistance to UV-degradation which is maintained at elevated temperatures. There is a further need to provide such aversive properties and UV protection at reduced processing complexity.

EP 3138898 A1 relates to water-soluble articles that include a water soluble or water dispersible film, where the film includes an aversive agent.

SUMMARY OF THE INVENTION

The present disclosure relates to a water-soluble film comprising a quinoliziumolate. The quinoliziumolate may be selected from those quinoliziumolates according to formula (I), formula (II), or a mixture thereof, where formula (I) is

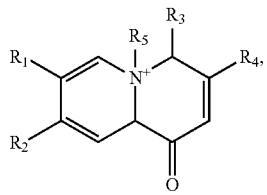

and formula (II) is

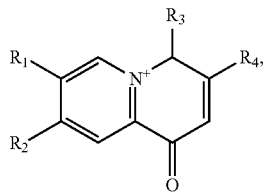

where R1 includes a chemical moiety selected from oxygen ion, hydroxyl, hydroxonium/hydronium, methanolate, carbonyl, fluoro-, chloro-, bromo-, iodo-, thio-, nitro-/azo-, amino-, silo-, phospho-, hydride, and mixtures thereof; R2 includes a chemical moiety selected from 2H-aziridine, oxirene, thiirene, azete, (di—)azetidene, dihydroazete, oxete, thiete(-ne), pyrolene and pyroazoles, furan, alkylfuran, oxathiols, dioxolenes, thiophene, oxazoles, thiazoles, thiadiazoles, thiazolidinones, succinimides, pyridine, pyran, alkylpyran, thiopyran, azepine, oxepine, thiepine, thiazine (-dioxides), thiomorpholine-dioxides, quinolines, azocines, azepines, sipro-alkenes, azospiro-alkenes, thiospiro-alkenes, and mixtures thereof; R3 includes a chemical moiety selected from hydroxyl, hydroxonium/hydronium, carbonyl, fluoro-, chloro-, bromo-, iodo-, thio-, nitro-/azo-, amino-, hydride, and mixtures thereof; R4 includes a chemical moiety selected from 2H-aziridine, oxirene, thiirene, azete, (di—)azetidene, dihydroazete, oxete, thiete(-ne), pyrolene and pyroazoles, furan, oxathiols, dioxolenes, thiophene, oxazoles, thiazoles, thiadiazoles, thiazolidinones, succinimides, pyridine, pyran, thiopyran, azepine, oxepine, thiepine, thiazine (-dioxides), thiomorpholine-dioxides, quinolines, azocines, azepines, sipro-alkenes, azospiro-alkenes, thiospiro-alkenes; R5 includes a chemical moiety selected from hydroxyl, hydroxonium/hydronium, carbonyl, fluoro-, chloro-, bromo-, iodo-, thio-, nitro-/azo-, amino-, silo-, phospho-, hydride, methyl, ethyl, propyl, butyl, pentyl, heptyl, octyl, nonyl-, and aromatic hydrocarbons; where the level of quinoliziumolate is from about 0.05 ppm to about 1.0 ppm as determined after storage of the water-soluble film for one month at 25° C. and 60% relative humidity.

The present disclosure further relates to unit dose articles that include such films.

The present disclosure further relates to processes that relate to such films.

DETAILED DESCRIPTION OF THE INVENTION

It has been surprisingly found that quinoliziumolate provides water-soluble films and unit dose articles comprising such films with improved thermostable UV protection and an acceptable bittering value at the same time. Without wishing to be bound by theory, since quinoliziumolate acts both as a thermally stable UV protective agent and a bittering agent, this reduces processing complexity and minimises instability of the film as there is a reduced need to add multiple materials. Whilst the bitter value of quinoliziumolate is not as high as Denatonium benzoate, it does elicit a bitter response.

The components of the present disclosure are described in more detail below.

Water-Soluble Film

The present disclosure relates to water-soluble films and unit dose articles comprising such films. The article may be in the form of a pouch. The film may form a compartment and may at least partly encapsulate a composition, for example a liquid composition. The film comprises quinoliziumolate, described in more detail below.

The water-soluble film may be characterized by an average thickness of from 80 µm to 200 µm. The average thickness of the film may be from 80 µm to 150 µm, or from 85 µm to 125 µm, or from 85 µm to 100 µm. The average thickness of the film may be about 85 µm.

It is understood that the thickness of a water-soluble film may change due to processing or converting operations, such as thermoforming into a mold or stretching from general film handling. Therefore, as used herein, "thickness" of a film means the thickness before the film has been subjected to any thermoforming, elastic strain, or plasticization techniques. For the removal of doubt, the thickness of the film may be determined prior to the film be formed into a unit dose article and/or a pouch. The average thickness is determined according to the method described below.

The film of the present invention is soluble or dispersible in water. Preferred films exhibit good dissolution in cold water, meaning unheated distilled water. Preferably such films exhibit good dissolution at temperatures 24° C., even more preferably at 10° C. By good dissolution it is meant that the film exhibits water-solubility of at least 50%, preferably at least 75% or even at least 95%, as measured, by the method set out here after using a glass-filter with a maximum pore size of 20 microns, described below. Water-solubility may be determined at 24° C., or preferably at 10° C. (see Methods).

Preferred film materials are preferably polymeric materials. The film material can, for example, be obtained by casting, blow-moulding, extrusion, or blown extrusion of the polymeric material, as known in the art. Preferably the film is obtained by an extrusion process or by a casting process.

Preferred polymers (including copolymers, terpolymers, or derivatives thereof) suitable for use as film material are selected from polyvinyl alcohols (PVA), polyvinyl pyrrolidone, polyalkylene oxides, acrylamide, acrylic acid, cellulose, cellulose ethers, cellulose esters, cellulose amides, polyvinyl acetates, polycarboxylic acids and salts, polyaminoacids or peptides, polyamides, polyacrylamide, copolymers of maleic/acrylic acids, polysaccharides including starch and gelatine, natural gums such as xanthum and carragum. More preferred polymers are selected from polyacrylates and water-soluble acrylate copolymers, methylcellulose, carboxymethylcellulose sodium, dextrin, ethylcellulose, hydroxyethyl cellulose, hydroxypropyl methylcellulose, maltodextrin, polymethacrylates, and most preferably selected from polyvinyl alcohols, polyvinyl alcohol copolymers and hydroxypropyl methyl cellulose (HPMC), and combinations thereof. Preferably, the polymers of the film material are free of carboxylate groups.

Preferably, the level of polymer in the film material, for example a PVA polymer, is at least 60%. The polymer can have any weight average molecular weight, preferably from about 1000 to 1,000,000, more preferably from about 10,000 to 300,000, yet more preferably from about 20,000 to 150,000.

Mixtures of polymers can also be used as the film material. This can be beneficial to control the mechanical and/or dissolution properties of the compartments or pouch, depending on the application thereof and the required needs. Suitable mixtures include for example mixtures wherein one polymer has a higher water-solubility than another polymer, and/or one polymer has a higher mechanical strength than another polymer. Also suitable are mixtures of polymers having different weight average molecular weights, for example a mixture of PVA or a copolymer thereof of a weight average molecular weight of about 10,000 to about 40,000, preferably about 20,000, and of PVA or copolymer thereof, with a weight average molecular weight of about 100,000 to about 300,000, preferably about 150,000. Also suitable herein are polymer blend compositions, for example comprising hydrolytically degradable and water-soluble polymer blends such as polylactide and polyvinyl alcohol, obtained by mixing polylactide and polyvinyl alcohol, typically comprising about 1-35% by weight polylactide and about 65% to 99% by weight polyvinyl alcohol. Preferred for use herein are polymers, preferably polyvinyl alcohol, which are from about 60% to about 99% hydrolysed, preferably from about 80% to about 99% hydrolysed, even more preferably from about 80% to about 90% hydrolysed, to improve the dissolution characteristics of the material. Preferred films are those supplied by Monosol (Merrillville, Ind., USA) under the trade references M8630, M8900, M8779, M8310, M9467, and PVA films of corresponding solubility and deformability characteristics. Other suitable films may include called Solublon® PT, Solublon® GA, Solublon® KC or Solublon KL from the Aicello Chemical Europe GmbH, the films VF-HP by Kuraray, or the films by Nippon Gohsei, such as Hi Selon. Suitable films include those supplied by Monosol for use in the following Procter and Gamble products: TIDE PODS, CASCADE ACTION PACS, CASCADE PLATINUM, CASCADE COMPLETE, ARIEL 3 IN 1 PODS, TIDE BOOST ORIGINAL DUO PACs, TIDE BOOST FEBREZE SPORT DUO PACS, TIDE BOOST VIVID WHITE BRIGHT PACS, DASH, FAIRY PLATINUM. It may be preferable to use a film that exhibits better dissolution than M8630 film, supplied by Monosol, at temperatures 24° C., even more preferably at 10° C.

Preferred water soluble films are those derived from a resin that comprises a blend of polymers, preferably wherein at least one polymer in the blend is polyvinyl alcohol. Preferably, the water-soluble film resin comprises a blend of PVA polymers. For example, the PVA resin can include at least two PVA polymers, wherein as used herein the first PVA polymer has a viscosity less than the second PVA polymer. A first PVA polymer can have a viscosity of at least 8 centipoise (cP), 10 cP, 12 cP, or 13 cP and at most 40 cP, 20 cP, 15 cP, or 13 cP, for example in a range of about 8 cP to about 40 cP, or 10 cP to about 20 cP, or about 10 cP to about 15 cP, or about 12 cP to about 14 cP, or 13 cP. Furthermore, a second PVA polymer can have a viscosity of at least about 10 cP, 20 cP, or 22 cP and at most about 40 cP, 30 cP, 25 cP, or 24 cP, for example in a range of about 10 cP to about 40 cP, or 20 to about 30 cP, or about 20 to about 25 cP, or about 22 to about 24, or about 23 cP. The viscosity of a PVA polymer is determined by measuring a freshly made solution using a Brookfield LV type viscometer with UL adapter as described in British Standard EN ISO 15023-2: 2006 Annex E Brookfield Test method. It is international practice to state the viscosity of 4% aqueous polyvinyl alcohol solutions at 20° C. All viscosities specified herein in cP should be understood to refer to the viscosity of 4% aqueous polyvinyl alcohol solution at 20° C., unless specified otherwise. Similarly, when a resin is described as having (or not having) a particular viscosity, unless specified otherwise, it is intended that the specified viscosity is the average viscosity for the resin, which inherently has a corresponding molecular weight distribution.

The individual PVA polymers can have any suitable degree of hydrolysis, as long as the degree of hydrolysis of the PVA resin is within the ranges described herein. Optionally, the PVA resin can, in addition or in the alternative, include a first PVA polymer that has a Mw in a range of about 50,000 to about 300,000 Daltons, or about 60,000 to about 150,000 Daltons; and a second PVA polymer that has a Mw in a range of about 60,000 to about 300,000 Daltons, or about 80,000 to about 250,000 Daltons. Of the total PVA resin content in the film described herein, the PVA resin can comprise about 30 to about 85 wt % of the first PVA polymer, or about 45 to about 55 wt % of the first PVA polymer. For example, the PVA resin can contain about 50 w. % of each PVA polymer, wherein the viscosity of the first PVA polymer is about 13 cP and the viscosity of the second PVA polymer is about 23 cP.

The film material herein can also comprise one or more additive ingredients. For example, the film preferably comprises a plasticizing agent. The plasticizing agent may comprise water, glycerol, ethylene glycol, diethylene glycol, propylene glycol, diproypylene glycol, sorbitol, or mixtures thereof. In some aspects, the film comprises from about 2% to about 35%, or from about 5% to about 25%, by weight of the film, a plasticizing agent selected from group comprising water, glycerol, diethylene glycol, sorbitol, and mixtures thereof. In some aspects, the film material comprises at least two, or preferably at least three, plasticizing agents. In some aspects, the film is substantially free of ethanol, meaning that the film comprises from 0% (including 0%) to about 0.1% ethanol by weight of the film. In some aspects, the plasticizing agents are the same as solvents found in an encapsulated liquid composition.

Other additives may include water and functional detergent additives, including surfactant, to be delivered to the wash water, for example, organic polymeric dispersants, etc. Additionally, the film may comprise an aversive agent, further described herein.

The water-soluble unit dose article may comprise an area of print. The water-soluble unit dose article may be printed using flexographic techniques, ink jet printing techniques or a mixture thereof. The printed are may be on the film, preferably on the outside of the film, within the film, on the inside of the film or a mixture thereof. The printed area may convey information such as usage instructions, chemical safety instructions or a mixture thereof. Alternatively, the entire surface of the pouch, or substantially the entire surface of the pouch is printed in order to make the pouch opaque. The print may convey an image that reduces the risk of confusion and hence accidental ingestion of the pouch.

Quinoliziumolate

The water-soluble film of the present invention comprises quinoliziumolate according to formula (I), formula (II), or a mixture thereof, wherein formula (I) is

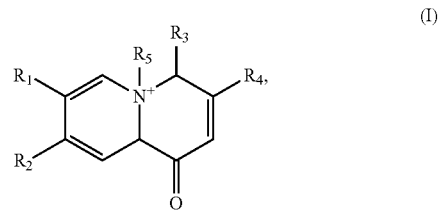

and formula (II) is

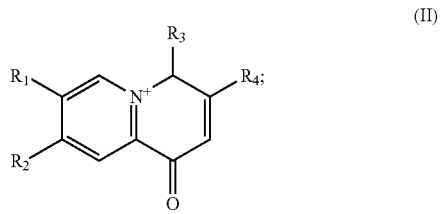

wherein R1 comprises a chemical moiety selected from the list consisting of oxygen ion, hydroxyl, hydroxonium/hydronium, methanolate, carbonyl, fluoro-, chloro-, bromo-,iodo-,thio-, nitro-/azo-, amino-, silo-, phospho-, hydride, and mixtures thereof; preferably R1 is selected from the list consisting of oxygen ion (carrying a negative charge), hydroxyl, hydroxonium/hydronium, carbonyl, fluoro-,chloro-, bromo-,iodo-, thio-, nitro-/azo-, amino-, phospho-, hydride; more preferably R1 is selected from the list consisting of oxygen ion, hydroxyl, hydroxonium/hydronium, methanolate, fluoro-,chloro-, bromo-,iodo-,thio-, nitro-/azo-, amino-, phospho-; even more preferably R1 is hydroxyl or oxygen ion;

R2 comprises a chemical moiety selected from the list consisting of 2H-aziridine, oxirene, thiirene,azete, (di—)azetidene, dihydroazete, azete, oxete, thiete(-ne), pyrolene and pyroazoles, furan, alkylfuran, oxathiols, dioxolenes, thiophene, oxazoles,thiazoles, thiadiazoles, thiazolidinones, succinimides, pyridine, pyran, alkylpyran, thiopyran, azepine, oxepine, thiepine, thiazine (-dioxides), thiomorpholine-dioxides, quinolines, azocines, azepines, sipro-alkenes,azospiro-alkenes, thiospiro-alkenes, and mixtures thereof; preferably R2 is selected from the list consisting of alkylfuran and alkylpyran; morepreferably R2 is methylfuran;

R3 comprises a chemical moiety selected from the list consisting of hydroxyl, hydroxonium/hydronium, carbonyl, fluoro-,chloro-, bromo-,iodo-,thio-, nitro-/azo-, amino-, hydride, and mixtures thereof; preferably R3 is selected from the list consisting of alkylhydroxyl, alky-.hydroxonium/alkylhydronium, alkylfluoro-, alkylchloro-, alkylbromo-,alkyliodo-, alkylthio-, alkylnitro-/ alkylazo-, alkylamino-, alkylphospho-, alkylhydride; more preferably R3 is selected from the list consisting of methylhydroxyl, methylhydroxonium/methylhydronium, methylfluoro-, methylchloro-, methylbromo-, methyliodo-,methylthio-, methylnitro-/methylazo-, methylamino-, methylphospho-;

R4 comprises a chemical moiety selected from the list consisting of 2H-aziridine, oxirene, thiirene,azete, (di—)azetidene, dihydroazete, azete, oxete, thiete(-ne), pyrolene and pyroazoles, furan, oxathiols, dioxolenes, thiophene, oxazoles,thiazoles, thiadiazoles,thiazolidinones, succinimides, pyridine, pyran, thiopyran, azepine, oxepine, thiepine, thiazine (-dioxides), thiomorpholine-dioxides, quinolines, azocines, azepines, sipro-alkenes,azospiro-alkenes, thiospiro-alkenes; preferably R4 is selected from alkylfuran and alkylpyran; more preferably R4 is methylfuran;

R5 comprises a chemical moiety selected from the list consisting of hydroxyl, hydroxonium/hydronium, carbonyl, fluoro-,chloro-, bromo-,iodo-,thio-, nitro-/azo-, amino-, silo-,phospho-, hydride, methyl, ethyl, propyl, butyl, pentyl, heptyl, octyl, nonyl-, and aromatic hydrocarbons; preferably R5 is selected from the list consisting of alkylhydroxyl, alkylhydroxonium/alkylhydronium; more preferably R5 is selected from the list consisting of methylhydroxyl, methylhydroxonium/ methylhydronium;

wherein the level of quinoliziumolate is from 0.05 ppm to 1.0 ppm, preferably from 0.08 to 0.8 ppm, more preferably from 0.1 to 0.7 ppm, even more preferably from 0.2 to 0.5 ppm by weight of the film as determined after storage of the water-soluble film for one month 25° C. and 60% relative humidity.

Especially preferred quinoliziumolates are selected from the quinoliziumolates

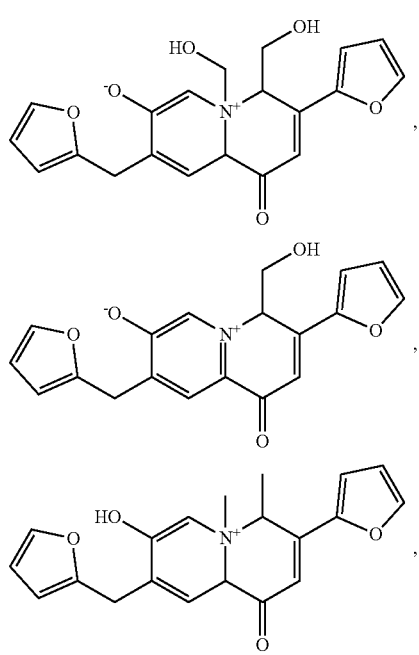

and mixtures thereof; most preferably the quinoliziumolate in the water-soluble film is

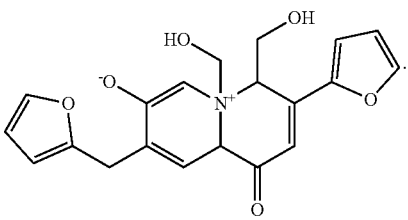

Water-soluble films comprising quinoliziumolate, according to the present invention, surprisingly provide the combination of adequate UV-protection and bittering properties. Because of the high thermostability, water-soluble films according to the present invention provide combined UV protection and adequate bittering properties over the entire film, also upon extended storage. Furthermore, because of the high thermostability, water-soluble films comprising quinoliziumolates according to the present invention allow for film processing at elevated temperatures.

Additional Aversive Agent

The films, unit dose articles, methods, and/or uses of the present disclosure may include one or more additional aversive agents different from quinoliziumolate. As used herein, an aversive agent is an agent that is intended to discourage ingestion and/or consumption of the unit dose articles described herein or components thereof, such as water-soluble films. An aversive agent may act by providing an unpleasant sensation, such as an unpleasant taste, when placed in the mouth or ingested. Such unpleasant sensations may include bitterness, pungency (or heat/spiciness), an unpleasant odor, sourness, coldness, and combinations thereof. An aversive agent may also act by causing humans and/or animals to vomit, for example via emetic agents. Suitable aversive agents include bittering agents, pungent agents, emetic agents, and mixtures thereof.

The level of aversive agent used within or on the unit dose articles or components thereof may be at least at an effective level, which causes the desired aversive effect, and may depend on the characteristics of the specific aversive agents, for example bitter value. The level used may also be at or below such a level that does not cause undesired transfer of the aversive agents to a human and/or animal, such as transfer to hands, eyes, skin, or other body parts. The amount present may be based on the particular aversive agent's potency such that greater than 50% of humans experience an aversive effect when exposed to the given amount of the aversive agent. The aversive agent may be present at a concentration which elicits repulsive behavior within a maximum time of six seconds in cases of oral exposure.

The aversive agent may be provided to the unit dose article or component thereof in any suitable manner. The aversive agent may be formulated into a film-forming material during manufacture of the film, or it may be provided after the film is manufactured, or even during or after the manufacture of the unit dose article. If the aversive agent is formulated into the water-soluble film as the film is being manufactured, the water-soluble film may comprise a substrate element and an aversive agent chemically coupled to the substrate element, for example as described in US2014/0371411A1. The aversive agent may be applied to a surface of the unit dose article or component thereof, for example by spraying, printing, atomizing, dusting, powdering, coating, painting, or otherwise depositing the aversive agent directly onto the water-soluble film and/or the finished unit dose article. The aversive agent may be provided in compositions encapsulated by water-soluble film, and may migrate to the film and/or to the surface of the film, which may be facilitated by the selection of certain solvents and/or plasticizers.

When a composition comprising the aversive agent is applied to the film and/or unit dose article, the composition may be non-aqueous so as to minimize dissolution of the film and/or article. Here, by non-aqueous it is meant that the composition may comprise less than about 20%, or less than about 15%, or less than about 10%, or less than about 5%, or less than about 1%, or about 0%, or 0%, by weight of the composition, of water. The composition may comprise up to about 100%, or 80%, or 60%, or 40%, or 35%, or 30% of the aversive agent. The composition may comprise from greater than 0% to about 100%, or from about 0.001% to about 80%, or from about 0.001% to about 60%, or from about 0.001% to about 40%, or from about 0.1% to about 35%, or from about 1% to about 30% by weight of the aversive agent.

The aversive agent may be provided in any suitable form. The aversive agent may be in the form of particles comprising the aversive agent, encapsulates comprising the aversive agent, a gel matrix comprising the aversive agent, or a combination thereof. In such forms, the aversive agent may be held within or on the carrier, within the encapsulate, and/or within the gel matrix until it is contacted with a relevant substrate, such as saliva, after which the aversive agent is released.

The aversive agent may be in the form of particles comprising a carrier and the aversive agent. The carrier may be selected from the group comprising carbonate, sulphate, zeolite, talc, clay, saccharides, polysaccharides, or mixtures thereof. The carrier may comprise a polysaccharide, which may be selected from maltodextrin, cellulose or a mixture thereof.

The carrier may form a matrix into which the aversive agent is absorbed. The aversive agent may be coated onto the carrier. The carrier may form a matrix into which the aversive agent is absorbed and the aversive agent is coated onto the carrier. For example, the aversive agent may be coated onto the carrier and then at least part of the aversive agent is absorbed into the carrier.

Wherein the aversive agent is in the form of a particle, the particle may be a spray-dry particle, an agglomerate, an extrudate, or a mixture thereof.

The aversive agent maybe in the form of a gel matrix comprising the aversive agent. A gel in this case means a composition of sufficiently high viscosity such that it substantially remains adhered to the water-soluble unit dose article until intended use. The gel matrix may comprise a wax, a saccharide, or a mixture thereof.

When the aversive agent is in the form of an encapsulate, the encapsulate may be a core and shell encapsulate, where the core comprises the aversive agent. The shell may comprise polyvinyl alcohol, melamine formaldehyde, polylactide, polyglycolide, gelatin, polyacrylate, shellac, zein, chitosan, wax, hydrogenated vegetable oil, polysaccharides paraffin and mixtures thereof. The shell may comprise a polylactide-polyglycolide copolymer. The shell may comprise a hydrogenated castor oil.

The aversive agent may be selected from the group comprising naringin; sucrose octaacetate; denatonium benzoate; capsicinoids (including capsaicin); vanillyl ethyl ether; vanillyl propyl ether; vanillyl butyl ether; vanillin propylene; glycol acetal; ethylvanillin propylene glycol acetal; gingerol; 4-(1-menthoxymethyl)-2-(3'-methoxy-4'-hydroxy-phenyl)-1,3-dioxolane; pepper oil; pepperoleoresin; gingeroleoresin; nonylic acid vanillylamide; jamboo oleoresin; Zanthoxylum piperitum peel extract; sanshool; sanshoamide; black pepper extract; chavicine; piperine; spilanthol; and mixtures thereof. Other suitable aversive agents are described in more detail below.

a. Bittering Agents

The aversive agent may comprise a bittering agent. The bittering agent may be present in and/or on the unit dose articles described herein and/or components thereof.

Non-limiting examples of suitable bittering agents include denatonium salts and derivatives thereof. The bittering agent may be a denatonium salt selected from the group consisting of denatonium chloride, denatonium citrate, denatonium saccharide, denatonium carbonate, denatonium acetate, denatonium benzoate, and mixtures thereof. The bittering agent may be denatonium benzoate, also known as phenylmethyl-2-[(2,6-dimethylphenyl)aminol-2-oxoethyl]-diethylammonium benzoate, CAS no. 3734-33-6. Denatonium benzoate is commercially sold as BITREX®, available from Macfarlan Smith, Edinburgh, Scotland, UK.

The bittering agent may be a natural bitter substance. The natural bitter substance may be selected from the group consisting of glycosides, isoprenoids, alkaloids, amino acids, and mixtures thereof. For example, suitable bittering agents also include Quercetin (3,3', 4', 5,7-pentahydroxyflavone); Naringin (4', 5,7-Trihydroxyflavanone-7-rhamnoglucoside); Aucubin;

Amarogentin; Dihydrofoliamentin; Gentiopicroside; Gentiopicrin; Swertiamarin; Swerosid; Gentioflavosid; Centaurosid; Methiafolin; Harpagoside; Centapikrin; Sailicin; Kondurangin; Absinthin; Artabsin; Cnicin; Lactucin; Lactucopicrin; Salonitenolid; α-thujone; ß-thujone; Desoxy Limonene; Limonin; Ichangin; iso-Obacunoic Acid; Obacunone; Obacunoic Acid; Nomilin; Ichangin; Nomilinoic acid; Marrubin; Pramarrubin; Carnosol; Carnosic acid; Quassin; Brucine; Quinine hydrochloride; Quinine sulfate; Quinine dihydrochloride; Columbine; Caffeine; Threonine; Methionine; Phenylalanine; Tryptophan; Arginine; Histidine; Valine; Aspartic acid; Sucrose octaacetate; and mixtures thereof. Other suitable bittering agents include quinine bisulfate and hop extract (e.g., humulone).

Other non-limiting examples of suitable bittering agents for use as described herein are described at BitterDB (http://bitterdb.agri.huji.ac.il/dbbitter.php), which is a free searchable database of bittering agents that holds over 680 bittering agents obtained from literature and the Merck Index and their associated 25 human bitter taste receptors (hT2Rs), and in the corresponding paper Ayana Wiener; Marina Shudler; Anat Levit; Masha Y. Niv. BitterDB: a database of bitter compounds. *Nucleic Acids Res* 2012, 40(Database issue): D413-419.

The bittering agent may exhibit a bitter value of greater than 1,000, or greater than 5,000, or greater than 10,000, or greater than 20,000, and/or less than 10,000,000, or less than 5,000,000, or less than 1,000,000, or less than 500,000, or less than 200,000, or less than 150,000, or less than 100,000. The bittering agent may exhibit a bitter value of from about 1,000 to about 10,000,000, or from about 5,000 to about 1,000,000, or from about 10,000 to about 200,000. The bitter value is measured using the standardized process set forth in the European Pharmacopoeia (5th Edition, Stuttgart 2005, Volume 1, General Monograph Groups, 2.8.15 Bitterness Value, p. 278).

The unit dose article or component thereof may comprise a sufficient amount of the bittering agent to provide a bitter taste, for example from about 0.00001% to about 1%, or from about 0.0001% to about 0.5%, or from about 0.001% to about 0.25%, or from about 0.01% to about 0.1% by weight of the unit dose article or component thereof.

The bittering agent may be present at a level of at least 10 ppb, or at least 50 ppb. The bittering agent may be present at a level of from about 10 ppb to about 10,000 ppm, or from about 50 ppb to about 5,000 ppm, or from about 50 ppb to about 1,000 ppm, or from about 100 ppb to about 500 ppm, or from about 10 ppm to about 250 ppm as determined after storage of the article and/or film for one month 25° C. and 60% relative humidity.

b. Pungent Agents

The aversive agent may comprise a pungent agent. Pungent agents provide pungency, which is the characteristic commonly referred to as spiciness, hotness, or "heat," often found in foods such as chili peppers.

Non-limiting examples of suitable pungent agents may include: capsicinoids (including capsaicin); vanillyl ethyl ether; vanillyl propyl ether; vanillyl butyl ether; vanillin propylene; glycol acetal; ethylvanillin propylene glycol acetal; capsaicin; gingerol; 4-(1-menthoxymethyl)-2-(3'-rnethoxy-4'-hydroxy-phenyl)-1, 3-dioxolane; pepper oil; pepper oleoresin; ginger oleoresin; nonylic acid vanillylamide; jamboo oleoresin; Zanthoxylum piperitum peel extract; sanshool; sanshoamide; black pepper extract; chavicine; piperine; spilanthol; and mixtures thereof. Other suitable pungent agents include polygodial, Tasmannia lanceolata extract, Capsicum extracts, or mixtures thereof. The pungent agent may comprise a capsaicinoid, for example capsaicin, dihydrocapsaicin, nordihydrocapsaicin, homodihydrocapsaicin, homocapsaicin, and/or nonivamide. The pungent agent may comprise capsaicin.

Commercially available suitable pungent agents include OPTAHEAT (Symise Flavors), HOTACT (Lipo Chemicals), and HEATENOL (Sensient Flavors).

The unit dose article and/or component thereof (e.g., water-soluble film) may comprise a sufficient amount of the pungent agent to deliver a pungent taste and/or pungent smell, for example a controlled level of pungency to a user (enough to deter ingestion but not so much as to make a human and/or animal physically ill or to accidentally transfer significant amounts to a user's hands). The article or component thereof may comprise greater than 0.0001%, or greater than 0.001%, or greater than 0.01%, or greater than 0.1%, and/or less than 20%, or less than 15%, or less than 10%, or less than 5%, or less than by 2%, or less than 1%, or less than 0.5%, by weight of the article or component, of the pungent agent. The article or component thereof may comprise from about 0.0001% to about 10%, or from about 0.001% to about 2%, or from about 0.01% to about 1%, or from about 0.1% to about 0.5%, by weight of the article or component, of the pungent agent. The pungent agent may be present at a level of at least 10 ppb, or at least 50 ppb. The pungent agent may be present at a level of from about 10 ppb to about 10,000 ppm, or from about 50 ppb to about 5,000 ppm, or from about 50 ppb to about 1,000 ppm, or from about 100 ppb to about 500 ppm, or from about 10 ppm to about 250 ppm as determined after storage of the article and/or film for one month 25° C. and 60% relative humidity.

The pungency of a pungent agent may be determined according to the well-known Scoville Scale and may be reported in Scoville heat units (SHU). The pungent agent may be selected from pungent agents having a pungency level of at least about 1,000,000 SHU, or at least about 5,000,000 SHU, or at least about 10,000,000 SHU, or at least about 15,000,000 SHU. For comparison, the pungency level of capsaicin is about 16,000,000 SHU. Pungency may also be measured by high performance liquid chromatography and determined in American Spice Trade Association (ASTA) pungency units. A measurement of one part capsaicin per million corresponds to about 15 Scoville units, and ASTA pungency units can be multiplied by 15 and reported as Scoville units.

Because it is desirable that the pungent agent be detectable in order to be an effective aversive agent, it is generally desirable that the pungency not be masked by other agents, such as cooling agents like menthol and the like. Therefore, the unit dose articles and/or components thereof may be free, for example comprising less than 5%, or less than 3%, or less than 1%, or less than 0.1%, or less than 0.01%, or less than 0.001%, or about 0%, or 0%, by weight of the article or component, of cooling agents, for example menthol and/or eucalyptus.

c. Emetic Agents

The aversive agent may comprise an emetic agent. There are two main types of emetic agents: 1) those that work directly on the gastrointestinal tract of humans and animals, and 2) those that work indirectly by stimulating the areas of the brain that control vomiting.

Non-limiting examples of suitable emetic agents that work directly on the gastrointestinal tracts are selected from the group consisting of: ipecac (ipecac syrup and/or ipecac powder) obtained from *Cephaelis ipecacuanha*, lobelia obtained from *Lobelia inflata*, mustard seed obtained from *Brassica juncea*, vomitoxin obtained from *Fusarium graminearum*, copper sulfate, and mixtures thereof. The aversive agent may comprise ipecac.

An example of an emetic agent that works indirectly by stimulating the areas of the brain that control vomiting is apomorphine (apomorphine hydrochloride).

Water-Soluble Unit Dose Article

The present disclosure relates to a water-soluble unit dose article. The article comprises a water-soluble or water-dispersible film, described in more detail below. The film may at least partially encapsulate a composition, for example a liquid composition comprising surfactant, described in more detail below. The composition may be a household care composition.

More specifically, the water-soluble unit dose article may comprise at least one water-soluble film shaped such that the unit-dose article comprises at least one internal compartment surrounded by the water-soluble film. The at least one compartment comprises the detergent or cleaning composition. The water-soluble film is sealed such that the detergent or cleaning composition does not leak out of the compartment during storage. However, upon addition of the water-soluble unit dose article to water, the water-soluble film dissolves and releases the contents of the internal compartment into the wash liquor. When the article, such as a pouch, is placed in water at 20° C., a liquid composition encapsulated therein may be retained within the pouch for at least 30 seconds.

The compartment should be understood as meaning a closed internal space within the unit dose article, which holds the composition. Preferably, the unit dose article comprises a water-soluble film. The unit dose article is manufactured such that the water-soluble film completely surrounds the composition and in doing so defines the compartment in which the composition resides. The unit dose article may comprise two films. A first film may be shaped to comprise an open compartment into which the composition is added. A second film is then laid over the first film in such an orientation as to close the opening of the compartment. The first and second films are then sealed together along a seal region. The film is described in more detail below.

The unit dose article may comprise more than one compartment, even at least two compartments, or even at least three compartments. The compartments may be arranged in superposed orientation, i.e. one positioned on top of the other. Alternatively, the compartments may be positioned in a side-by-side orientation, i.e. one orientated next to the other. The compartments may even be orientated in a 'tyre and rim' arrangement, i.e. a first compartment is positioned next to a second compartment, but the first compartment at least partially surrounds the second compartment, but does not completely enclose the second compartment. Alternatively one compartment may be completely enclosed within another compartment.

Wherein the unit dose article comprises at least two compartments, one of the compartments may be smaller than the other compartment. Wherein the unit dose article comprises at least three compartments, two of the compartments may be smaller than the third compartment, and preferably the smaller compartments are superposed on the larger compartment. The superposed compartments preferably are orientated side-by-side.

In a multi-compartment orientation, the composition according to the present invention may be comprised in at least one of the compartments. It may for example be comprised in just one compartment, or may be comprised in two compartments, or even in three compartments.

Each compartment may comprise the same or different compositions. The different compositions could all be in the same form, for example they may all be liquid, or they may be in different forms, for example one or more may be liquid and one or more may be solid.

A first compartment may contain a liquid composition, and a second compartment may contain a solid composition, for example a granular or powdered composition. The detergent or cleaning composition may be present in one compartment or may be present in more than one compartment.

The water-soluble unit dose article may comprise an air bubble. The water-soluble unit dose article may be transparent, translucent, opaque, or combinations thereof.

Composition

The unit dose articles described herein may comprise a composition, such as a detergent or cleaning composition. The unit dose articles may contain a liquid composition. The liquid composition may be at least partially encapsulated by the water-soluble film. By 'liquid' we herein mean any composition capable of wetting and treating a substrate and encompasses forms such as dispersions, gels, pastes and the like. A dispersion, for example, is a liquid comprising solid or particulate matter contained therein. The liquid composition may also include gases in suitably subdivided form. At least parts of the composition, e.g., the detergent or cleaning composition, may be in the form of a powder, a compacted powder, a liquid, or a mixture thereof.

The unit dose articles described herein may comprise the detergent or cleaning composition comprising surfactant, for example by encapsulating the composition in a water-soluble or water-dispersible film. The detergent or cleaning composition may be a fabric detergent or cleaning composition, an automatic dishwashing detergent or cleaning composition or a mixture thereof.

By "fabric detergent or cleaning composition" we herein mean compositions that provide cleaning benefit to fabrics, care benefit to fabrics or a mixture thereof. The fabric detergent or cleaning composition may provide a cleaning benefit selected from stain removal, stain-repellency, anti-soil-redeposition, brightening, whitening dirt removal, malodour reduction or mixtures thereof. The fabric detergent or cleaning composition may provide a care benefit selected from softening, freshness, anti-wrinkling, anti-colour fading, dye transfer inhibition, anti-static or mixtures thereof.

By "automatic dishwashing detergent or cleaning composition" we herein mean automatic dishwashing compositions that provide cleaning benefits, care benefits or a mixture thereof. "Automatic dishwashing care benefits" refers to any automatic dishwashing composition that can provide shine, fast drying, metal, glass or plastic protection benefits.

The liquid composition composition may comprise anionic surfactants, non-ionic surfactants, cationic surfactants, polyethylene glycol polymers, ethoxylated polyethyleneimines, rheology modifier, hueing dyes, perfumes, perfume microcapsules, chelants, enzymes, silicones, polyolefin waxes, latexes, oily sugar derivatives, cationic polysaccharides, polyurethanes, fatty acids, enzyme stabilizing systems; antioxidants, opacifier, pearlescent agent, deposition aid, builder, bleaching agent, bleach activator, bleach catalyst, organic shine polymers, surface modifying polymers, metal care agents, metal salts, anti-corrosion agents and mixtures thereof.

The liquid composition may comprise between 10% and 60%, preferably between 15% and 55%, more preferably between 20% and 50%, most preferably between 25% and 45% by weight of the laundry detergent composition of a non-soap surfactant. Preferably, the non-soap surfactant comprises an anionic surfactant and a non-ionic surfactant. More preferably, the weight ratio of anionic surfactant to non-ionic surfactant is from 1:2 to 20:1, preferably from 1:1 to 15:1, more preferably from 1.5:1 to 10:1, most preferably from 5:1 to 10:1.

The non-soap anionic surfactant is preferably selected from linear alkylbenzene sulphonate, alkyl sulphate, alkoxylated alkyl sulphate or a mixture thereof. Preferably, the alkoxylated alkyl sulphate is an ethoxylated alkyl sulphate preferably with an average degree of ethoxylation of between 0.5 and 4, preferably between 1 and 4, more preferably between 2 and 4, most preferably about 3.

Preferably, the weight ratio of linear alkylbenzene sulphonate to alkoxylated alkyl sulphate is between 15:1 and 1:3, preferably 10:1 and 1:2, more preferably 5:1 and 1:1, even more preferably 3:1 and 1:1, most preferably 2:1 and 1:1.

The non-ionic surfactant may be selected from a fatty alcohol alkoxylate, an oxo-synthesised fatty alcohol alkoxylate, Guerbet alcohol alkoxylates, alkyl phenol alcohol alkoxylates, alkyl polyglucoside or a mixture thereof. Preferably, the non-ionic surfactant comprises a fatty alcohol ethoxylate non-ionic surfactant. Even more preferably the nonionic surfactant consists of a fatty alcohol ethoxylate surfactant.

Suitable fatty alcohol ethoxylate nonionic surfactants include the condensation products of aliphatic alcohols with from 1 to 25 moles of ethylene oxide. The alkyl chain of the aliphatic alcohol can either be straight or branched, guerbet, primary or secondary, and generally contains from 8 to 22 carbon atoms. The starting alcohol can be naturally derived, e.g. starting from natural oils, or synthetically derived, e.g. alcohols obtained for from for example oxo-, modified oxo- or Fischer-Tropsch processes. Examples of oxo-process derived fatty alcohols include the Lial and Isalchem fatty alcohols ex Sasol company and Lutensol fatty alcohols ex BASF company. Examples of modified-oxo process derived fatty alcohols include the Neodol fatty alcohols ex Shell company. Fischer-Tropsch derived fatty alcohols include Safol fatty alcohols ex Sasol company. The alkoxylate chain of fatty alcohol ethoxylates is made up solely of ethoxylate groups.

Preferably, the fatty alcohol ethoxylate non-ionic surfactant comprises on average between 8 and 18, more preferably between 10 and 16 even more preferably between 12 and 15 carbon atoms in the alcohol carbon chain, and on average between 5 and 12, preferably between 6 and 10, more preferably between 7 and 8 ethoxy units in the ethoxylation chain.

Preferably, the weight ratio of linear alkylbenzene sulphonate to non-ionic surfactant is between 2:1 to 20:1 preferably 2:1 and 10:1; more preferably 5:1 and 10:1.

Preferably, the weight ratio of alkoxylated alkyl sulphate to non-ionic surfactant is between 2:1 and 20:1 preferably between 2:1 and 10:1 more preferably between 2:1 and 5:1.

Preferably, the weight ratio of linear alkylbenzene sulphonate to fatty alcohol ethoxylate non-ionic surfactant is between 2:1 to 20:1 preferably 2:1 and 10:1; more preferably 5:1 and 10:1.

Preferably, the weight ratio of alkoxylated alkyl sulphate to fatty alcohol ethoxylate non-ionic surfactant is between 2:1 and 20:1 preferably between 2:1 and 10:1 more preferably between 2:1 and 5:1.

Preferably the liquid laundry detergent composition further comprises between 1.5% and 20%, more preferably between 2% and 15%, even more preferably between 3% and 10%, most preferably between 4% and 8% by weight of the liquid detergent composition of soap, preferably a fatty acid salt, more preferably an amine neutralized fatty acid salt, wherein preferably the amine is an alkanolamine more preferably selected from monoethanolamine, diethanolamine, triethanolamine or a mixture thereof, more preferably monoethanolamine.

The detergent or cleaning composition may comprise an enzyme. The enzyme may be selected from hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof.

The detergent or cleaning composition may comprise a polymer. The polymer may be selected from carboxylate polymers, polyethylene glycol polymers, terephthalate polymers, amine polymers, cellulosic polymers, dye transfer inhibition polymers, dye lock polymers such as a condensation oligomer produced by condensation of imidazole and epichlorhydrin, optionally in ratio of 1:4:1, hexamethylenediamine derivative polymers, ethoxylated polyethyleneimines and any combination thereof.

Other polymers include hydroxyethyl cellulose polymer. Preferably, the hydroxyethyl cellulose polymer is derivatised with trimethyl ammonium substituted epoxide. The cellulose polymer may have a molecular weight of between 100,000 and 800,000 daltons. The hydroxyethyl cellulose polymer may be added to the composition as a particle. It may be present in the composition of the particle or may be also be present as a liquid, or a mixture thereof.

The detergent or cleaning composition may comprise a rheology modifier. The rheology modifier can be selected from the group consisting of non-polymeric crystalline hydroxy-functional materials, polymeric rheology modifiers or mixtures thereof. Specific examples of suitable crystalline, hydroxyl-containing rheology modifiers include castor oil and its derivatives. Also practical are hydrogenated castor oil derivatives such as hydrogenated castor oil and hydrogenated castor wax.

The detergent or cleaning composition may comprise a builder. Suitable builders include polycarboxylate builders include cyclic compounds, particularly alicyclic compounds. Particularly suitable are citrate builders, e.g., citric acid and soluble salts thereof, particularly sodium salts thereof. The builder may be selected from aminocarboxylate builders, preferably selected from salts of MGDA (methyl-glycine-diacetic acid), GLDA (glutamic-N,N— diacetic acid), EDDS (ethylene diamine disuccinates), iminodisuccinic acid (IDS), and carboxymethyl inulin.

The detergent or cleaning composition may comprise a bleaching agent. Bleaching agents may comprise chlorine bleaches, oxygen bleaches, or mixtures thereof. The bleach may be selected from sodium perborate monohydrate, sodium perborate tetrahydrates, sodium percarbonate, and mixtures thereof.

The detergent or cleaning composition may comprise a peroxyacid bleach precursors, preferably selected from precursors of perbenzoic acid, cationic peroxyacid precursors, peracetic acid, sodium acetoxybenzene sulfonate, pentaacetylglucose, sodium 3,5,5-trimethylhexanoyloxybenzene sulfonate (iso-NOBS), sodium nonanoyloxybenzene sulfonate (NOBS), amide substituted alkyl peroxyacid precursors, benzoxazin peroxyacid precursors and mixtures thereof. The bleach may comprise ε-phthalimidoperoxycaproic acid[phthaloiminoperoxyhexanoic acid (PAP).

Preferably, if the detergent or cleaning composition comprises an automatic dishwashing composition, the automatic dishwashing composition is phosphate free, or substantially phosphate free.

The detergent or cleaning composition may comprise a hueing dye, a brightener or a mixture thereof.

Preferably the detergent or cleaning composition comprises a non-aqueous solvent, preferably between 5% and 30%, more preferably between 7% and 25% by weight of the detergent or cleaning composition of a non-aqueous solvent. Preferably, the non-aqueous solvent is selected from glycerol, ethylene glycol, 1,3 propanediol, 1,2 propanediol, tetramethylene glycol, pentamethylene glycol, hexamethylene glycol, 2,3-butane diol, 1,3 butanediol, diethylene glycol, triethylene glycol, polyethylene glycol, glycerol formal dipropylene glycol, polypropylene glycol, dipropylene glycol n-butyl ether, and mixtures thereof.

The detergent or cleaning composition may comprise water, preferably from 0.1% to 20%, more preferably from 0.5% to 15%, most preferably from 1% to 13.5% by weight of the detergent or cleaning composition of water.

Process for Making

The present disclosure further relates to a process of forming a pouch from a water-soluble or water-dispersible film and at least partially encapsulating a liquid composition with the film to form a unit dose article.

Suitable films are described above. The film may be characterized by an average thickness of from about 80 μm to about 200 μm, or from about 85 μm to about 125 μm, from about 90 μm to about 110 μm, or even about 100 μm. The method for determining the average thickness of the film is provided below.

The film comprises quinoliziumolate. The film may comprise an additional aversive agent. Quinoliziumolate and the optional additional aversive agent may be directly formulated into the film. The aversive agent may be provided to the film prior to pouch formation, or the aversive agent may be provided to the finished unit dose article. The aversive agent may be applied to a surface of the unit dose article or component thereof, for example by spraying, printing, atomizing, dusting, powdering, coating, painting, or otherwise depositing the aversive agent directly onto the water-soluble film and/or the finished unit dose article.

The process of the present disclosure may be continuous or intermittent. The process comprises the general steps of forming an open pouch, preferably by forming a water-soluble film into a mould to form said open pouch, filling the open pouch with a composition, preferably the liquid composition, closing the open pouch filled with a composition, preferably using a second water-soluble film to form the unit dose article. The second film may also comprise compartments, which may or may not comprise compositions. Alternatively, the second film may be a second closed pouch containing one or more compartments, used to close the open pouch. Preferably, the process is one in which a web of unit dose article is made, said web is then cut to form individual unit dose articles.

Alternatively, the first film may be formed into an open pouch comprising more than one compartment. In which case, the compartments formed from the first pouch may are in a side-by-side or 'tire and rim' orientation. The second film may also comprise compartments, which may or may not comprise compositions. Alternatively, the second film may be a second closed pouch used to close the multicompartment open pouch.

The unit dose article may be made by thermoforming, vacuum-forming, or a combination thereof. Thermoforming is preferred as it allows for greater processing flexibility.

For efficient thermoforming, thermoforming at a temperature higher than 140° C., or higher than 160° C., or higher than 180° C., is preferred. Unit dose articles may be sealed using any sealing method known in the art to at least partially encapsulate a liquid composition in the water-soluble film. Suitable sealing methods may include heat sealing, solvent sealing, pressure sealing, ultrasonic sealing, pressure sealing, laser sealing or a combination thereof.

The unit dose articles may be dusted with a dusting agent. Dusting agents can include talc, silica, zeolite, carbonate or mixtures thereof.

Use of Film

The present disclosure further relates to a use of a water-soluble film comprising a quinoliziumolate to improve UV-protection and to provide acceptable bittering to said film or to a unit dose article comprising said film.

Method of Use

The present disclosure also relates to a method of doing laundry comprising the steps of diluting a water-soluble unit dose article according to the present invention in water by a factor of at least 400 to form a wash liquor and then washing fabrics with said wash liquor.

The unit dose article of the present disclosure may be used alone in the wash operation or may be used in conjunction with other laundry additives such as fabric softeners (such as the commercially available DOWNY) or fabric stain removers. The unit dose article may be used in conjunction with fragrance boosting compositions such as commercially available LENOR UNSTOPABLES.

METHODS

Method to Determine Water Solubility

Water solubility is calculated using Chemdraw Professional v. 15.1.0.144, 1998-2016. Generally, the technique rely on the well-established Joback fragmentation techniques to derive aqueous solubility from chemical structure information.

Method to Determine Dissolution 50 grams ±0.1 gram of film material is added in a pre-weighed 400 ml beaker and 245 ml±1 ml of distilled water is added. This is stirred vigorously on a magnetic stirrer, labline model No. 1250 or equivalent and 5 cm magnetic stirrer, set at 600 rpm, for 30 minutes at 24° C. Then, the mixture is filtered through a folded qualitative sintered-glass filter with a pore size as defined above (max. 20 micron). The water is dried off from the collected filtrate by any conventional method, and the weight of the remaining material is determined (which is the dissolved or dispersed fraction). Then, the percentage solubility or dispersability can be calculated.

Method for Determining Average Film Thickness

Preferably, film thickness is measured according to ASTM D6988-13.

Alternatively, film thickness is measured according to the following method. Thickness testing is performed on a Thwing-Albert (West Berlin, N.J., USA), Model 89-100, thickness tester machine.

The PVA film may be prepared by storing the film at 22° C. (+/−3° C.) and at 45% Relative Humidity (+/−5%) for at least 24 hours prior to testing. Gloves are used to handle the film; there should be minimal handling, and creases and tears should be avoided. A piece of film, 100 mm×100 mm if possible, should be cut and prepared. A marker is used to lightly mark multiple dots that are equally spaced (approx. 10 mm apart and off-set, if possible) on the film. For example, 25 and/or 46 spots may be marked.

The thickness testing machine is turned on, warmed up, and prepared for measurements according to the manufacturer's instructions. The film sample is placed between the base of the equipment and the sensing probe (anvil). The first spot to be measured is placed in the middle of the metal base so that it is able to be targeted with the anvil. The Test button is pressed, and the anvil lowers. When the test is complete, note the thickness. Position and measure the second spot, and subsequent spots, accordingly, noting the thicknesses for each. After all the measurements have been taken, the statistics button may be used to determine the average thickness for the sample. Prior to measuring a second film sample, the machine should be cleared to reset the machine's memory.

Method for Measuring Presence/Migration of Aversive Agent

To determine the presence and/or amount of quinoliziumolate or additional aversive agent present on the surface of the film, sensory or analytical techniques may be employed. A suitable sensory technique (e.g., via taste in controlled circumstances) is disclosed in WO2014/026855 A1, assigned to Henkel AG & Co.

The aversive agent may be extracted from the surface via the following method. The unit dose pouch is held with tweezers at the seal. The surface of each side of the pouch is rinsed 10 times, with 4 to 5 mL of methanol used in each rinse cycle and collected. After rinsing, the methanol solution is transferred to a glass vial, and the methanol is evaporated. The remaining extract is then dissolved in the appropriate solvent needed for the analytical method.

Aversive agents can be assayed via standard methods known to those skilled in the art. Analytical techniques may include chromatography or spectroscopic techniques known to one skilled in the art. For example, suitable methods are disclosed in Falkner et al., Journal of Chromatography A. 715 (1995) 189-194, and in R. Bucci et al., Talanta 68 (2006) 781-790.

EXAMPLES

The water solubility and degradation of 6 components with UV filtering properties are described in Table 1. All examples Ex. 1-6 provide UV protection due to the presence of aromatic ring structures. Ex. 1-3 according to the present invention exhibits UV-absorbance at a wavelength between 170-300 nm based on computation chemistry (Gaussian 09, Revision A.02, M. J. Frisch et al., Gaussian, Inc., Wallingford Conn., 2016).

TABLE 1

Water solubility and degradation properties of UV protective agents ex. 1-6.

| Example | Molecule | Water Solubility LogS | Thermostability |
| --- | --- | --- | --- |
| Ex. 1 | Quinolizinium-I | −0.9 | High [a] |
| Ex. 2 | Quinolizinium-II+ | −1.4 | High [a] |
| Ex. 3 | Quinolizinium-III | −2.3 | High [a] |
| Ex. 4* | Butyloctyl Benzoate | −6.1 | Low [b] |
| Ex. 5* | Padimate O | −3.8 | Low [b] |
| Ex. 6* | Padimate A | −4.5 | Low [c] |

*Comparative examples
[a] Based on Sallay, Istvan S. in U.S. Pat. No. 3,267,107.
[b] Based on Lewin, Anita H., and Louise Fudala. "Preparation and investigation of [14C] padimate-O and [14C] N-nitroso-N-nor-padimate-O." Journal of Labelled Compounds and Radiopharmaceuticals 36.7 (1995): 637-643.
[c] Based on Yadav, Vasanti G., and S. B. Chandalia. "An efficient method for synthesis of 2-ethyl hexyl-4-methoxy cinnamate: A raw material for cosmetic industry." Indian Journal of Chemical Technology (1999): 6, 19-23.

The high thermostability of Ex.1 to 3 was assessed based on the melting point in the range of 233-334° C. However, comparative examples 4-6 exhibit degradation in the form of hydrolysis already at 25-28° C. As such, when present in a water-soluble film, degradation of Ex. 4-6 can already occur when exposed to humid air at or near 25° C. Ex. 1-3, in accordance to the present invention, have very good thermostability and hence are suitable UV protective agents which can be processed in water-soluble films handled at elevated temperatures such as the thermoforming process. As described in Table 2, examples 1-3 also exhibit adequate bittering. As a reference for bitterness, the bittering standard quinine (ex. 7) was used. A bittering index of a compound X, is defined by the formula:

$$\text{Bittering Index}(X) = \text{Log}\left(\frac{\text{Molar Detection threshold}(X)}{\text{Molar Detection Threshold (Quinine)}}\right)$$

TABLE 2

Bittering values of ex. 1-3 and comparative examples 7. Lower bittering values correspond to stronger bittering properties.

| Example | Molecule | Bittering index |
| --- | --- | --- |
| Ex. 1 | Quinolizinium-I | −1 [c] |
| Ex. 2 | Quinolizinium-II+ | |
| Ex. 3 | Quinolizinium-III | |
| Ex. 7* | Quinine | 0 [d] |

*Comparative examples
[c] Empirically determined by Frank, O., & Hofmann, T. (2002) in "Reinvestigation of the chemical structure of bitter-tasting quinizolate and homoquinizolate and studies on their Maillard-type formation pathways using suitable 13C-labeling experiments". Journal of agricultural and food chemistry, 50(21), 6027-6036.
[d] Empirically determined by Meyerhof, Wolfgang, et al. (2010) in "The molecular receptive ranges of human TAS2R bitter taste receptors." Chemical senses 35.2: 157-170.

Therefore, water-soluble films comprising ex. 1-3 according to the present invention surprisingly provide the combination of adequate UV-protection and bittering properties. Because of the high thermostability, water-soluble films according to the present invention provide combined UV protection and bittering properties over the entire film, also upon extended storage. Furthermore, because of the high thermostability, water-soluble films comprising quinoliziumolates according to the present invention allow for film processing at elevated temperatures.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A water-soluble film comprising a quinoliziumolate, wherein said quinoliziumolate is selected from those quinoliziumolates according to formula (I),
wherein formula (I) is

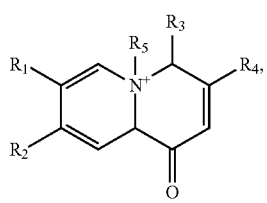

wherein $R_1$ comprises a chemical moiety selected from the group consisting of oxygen ion, hydroxyl, hydroxonium/hydronium, methanolate, carbonyl, fluoro-, chloro-, bromo-, iodo-, thio-, nitro-/azo-, amino-, silo-, phospho-, hydride, and mixtures thereof;

$R_2$ comprises a chemical moiety selected from the group consisting of 2H-aziridine, oxirene, thiirene, azete, (di—)azetidene, dihydroazete, oxete, thiete(-ne), pyrolene, pyroazoles, furan, alkylfuran, oxathiols, dioxolenes, thiophene, oxazoles, thiazoles, thiadiazoles, thiazolidinones, succinimides, pyridine, pyran, alkylpyran, thiopyran, azepine, oxepine, thiepine, thiazine (-dioxides), thiomorpholine-dioxides, quinolines, azocines, azepines, spiro-alkenes, azospiro-alkenes, thiospiro-alkenes, and mixtures thereof;

$R_3$ comprises a chemical moiety selected from the group consisting of hydroxyl, hydroxonium/hydronium, carbonyl, fluoro-, chloro-, bromo-, iodo-, thio-, nitro-/azo-, amino-, hydride, and mixtures thereof;

$R_4$ comprises a chemical moiety selected from the group consisting of 2H-aziridine, oxirene, thiirene, azete, (di—)azetidene, dihydroazete, oxete, thiete(-ne), pyrolene and pyroazoles, furan, oxathiols, dioxolenes, thiophene, oxazoles, thiazoles, thiadiazoles, thiazolidinones, succinimides, pyridine, pyran, thiopyran, azepine, oxepine, thiepine, thiazine (-dioxides), thiomorpholine-dioxides, quinolines, azocines, azepines, spiro-alkenes, azospiro-alkenes, thiospiro-alkenes;

$R_5$ comprises a chemical moiety selected from the group consisting of hydroxyl, hydroxonium/hydronium, carbonyl, fluoro-, chloro-, bromo-, iodo-, thio-, nitro-/azo-, amino-, silo-, phospho-, hydride, methyl, ethyl, propyl, butyl, pentyl, heptyl, octyl, nonyl-, and aromatic hydrocarbons;

wherein the level of quinoliziumolate is from about 0.05 ppm to about 1.0 ppm as determined after storage of the water-soluble film for one month at 25° C. and 60% relative humidity.

2. The water-soluble film according to claim 1, wherein the quinoliziumolate is present at a level of from about 0.08 to about 0.8 ppm, as determined after storage of the water-soluble film for one month at 25° C. and 60% relative humidity.

3. The water-soluble film according to claim 2, wherein the quinoliziumolate is present at a level of from about 0.1 to about 0.7 ppm, as determined after storage of the water-soluble film for one month at 25° C. and 60% relative humidity.

4. The water-soluble film according to claim 3, wherein the quinoliziumolate is present at a level of from about 0.2 to about 0.5 ppm as determined after storage of the water-soluble film for one month 25° C. and 60% relative humidity.

5. The water-soluble film according to claim 1,
wherein $R_1$ is selected from the group consisting of oxygen ion, hydroxyl, hydroxonium/hydronium, carbonyl, fluoro-, chloro-, bromo-, iodo-, thio-, nitro-/azo-, amino-, phospho-, hydride;
wherein $R_1$ is selected from the group consisting of alkylfuran and alkylpyran;
wherein $R_3$ is selected from the group consisting of alkylhydroxyl, alky.hydroxonium/alkylhydronium, alkylfluoro-, alkylchloro-, alkylbromo-, alkyliodo-, alkylthio-, alkylnitro-/alkylazo-, alkylamino-, alkylphospho-, alkylhydride;
wherein $R_4$ is selected from group consisting of alkylfuran and alkylpyran;
wherein $R_5$ is selected from the group consisting of alkylhydroxyl, alkylhydroxonium/alkylhydronium.

6. The water-soluble film according to claim 1, wherein the quinoliziumolate is selected from the quinoliziumolates,

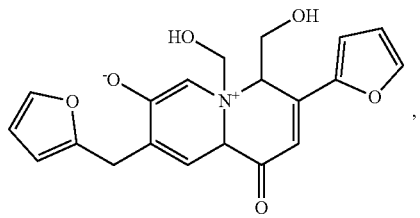

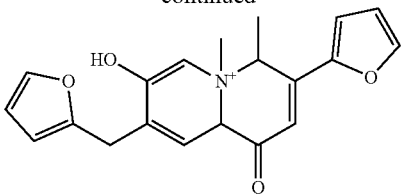

and mixtures thereof.

7. The water-soluble film according to claim 1, wherein the film comprises a polyvinyl alcohol polymer.

8. The water-soluble film according to claim 1, wherein the film further comprises an additional aversive agent selected from the group consisting of: naringin; sucrose octaacetate; denatonium benzoate; capsicinoids; vanillyl ethyl ether; vanillyl propyl ether; vanillyl butyl ether; vanillin propylene; glycol acetal; ethylvanillin propylene glycol acetal; gingerol; 4-(1-menthoxymethyl)-2-(3'methoxy-4'-hydroxy-phenyl)-1, 3-dioxolane; pepper oil; pepperoleoresin; gingeroleoresin; nonylic acid vanillylamide; jamboo oleoresin; Zanthoxylum piperitum peel extract; sanshool; sanshoamide; black pepper extract; chavicine; piperine; spilanthol; and mixtures thereof.

9. A unit dose article comprising the water-soluble film according to claim 1, wherein said unit dose article at least partly encapsulates a liquid composition comprising surfactant.

10. A unit dose article according to claim 9, wherein the average thickness of the film is from about 80 μm to about 150 μm.

11. A unit dose article according to claim 10, wherein the average thickness of the film is from about 85 μm to about 125 μm.

12. A unit dose article according to claim 11, wherein the average thickness of the film is from about 85 μm to about 100 μm.

13. A unit dose article according to claim 12, wherein the average thickness of the film is about 85 μm.

14. A unit dose article according to claim 9, wherein the unit dose article further comprises a bittering agent in an amount of from about 10 ppb to about 10,000 ppm, as determined after storage of the unit dose article for one month at 25° C. and 60% relative humidity.

15. A unit dose article according to claim 9, wherein the liquid composition comprises between 10% and 60%, by weight of the liquid composition of a non-soap surfactant.

16. A unit dose article according to claim 15 wherein the non-soap surfactant comprises an anionic surfactant and a non-ionic surfactant,
wherein the weight ratio of anionic surfactant to non-ionic surfactant is from 1:2 to 20:1.

17. A unit dose article according to claim 9, wherein the unit dose article comprises at least two compartments.

18. A unit dose article according to claim 17, wherein a first compartment contains the liquid composition, and wherein a second compartment contains a solid composition.

19. A process of forming a unit dose article, the process comprising the steps of:
providing a water-soluble film according to claim 1;
thermoforming the water-soluble film; and
at least partly encapsulating a liquid composition with the film.

20. The process according to claim 19, wherein during thermoforming, the water-soluble film has a temperature higher than 140° C.

* * * * *